(12) United States Patent
Abdullah et al.

(10) Patent No.: US 11,406,353 B2
(45) Date of Patent: Aug. 9, 2022

(54) DEVICE FOR UTILIZING TRANSMISSION ULTRASONOGRAPHY TO ENABLE ULTRASOUND-GUIDED PLACEMENT OF CENTRAL VENOUS CATHETERS

(71) Applicant: The Johns Hopkins University, Baltimore, MD (US)

(72) Inventors: Fizan Abdullah, Baltimore, MD (US); Seth Goldstein, Baltimore, MD (US); Emad Boctor, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 266 days.

(21) Appl. No.: 16/456,732

(22) Filed: Jun. 28, 2019

(65) Prior Publication Data
US 2019/0380678 A1 Dec. 19, 2019

Related U.S. Application Data

(63) Continuation of application No. 14/916,260, filed as application No. PCT/US2014/049353 on Aug. 1, 2014, now abandoned.
(Continued)

(51) Int. Cl.
*A61B 8/08* (2006.01)
*A61B 8/12* (2006.01)
*A61B 8/00* (2006.01)

(52) U.S. Cl.
CPC .............. *A61B 8/12* (2013.01); *A61B 8/0841* (2013.01); *A61B 8/4218* (2013.01); *A61B 8/445* (2013.01); *A61B 8/4483* (2013.01)

(58) Field of Classification Search
CPC ....... A61B 8/0841; A61B 8/12; A61B 8/4218; A61B 8/445; A61B 8/4483
See application file for complete search history.

(56) References Cited

U.S. PATENT DOCUMENTS

| 5,228,176 A | 7/1993 | Bui et al. |
| 6,039,693 A | 3/2000 | Seward et al. |

(Continued)

FOREIGN PATENT DOCUMENTS

| WO | WO-2005007228 A1 * | 1/2005 | ........ A61M 25/0082 |
| WO | 2005117710 A2 | 12/2005 | |

OTHER PUBLICATIONS

Skippen P., et al., "Ultrasound Guidance for Central Vascular Access in the Pediatric Emergency Department," Pediatric Emergency Care, Mar. 2007, vol. 23 (3), pp. 203-207.
(Continued)

*Primary Examiner* — Rochelle D Turchen
(74) *Attorney, Agent, or Firm* — Harrity & Harrity, LLP

(57) ABSTRACT

Ultrasound is typically performed with the use of an external transcutaneous probe that emits ultrasonic energy and measures the timing of reflected waves, thus allowing measurement of fluid flow or formation of a two-dimensional image. Clinically, the modality is limited by attenuation of the signal with increasing depth of penetration of the ultrasound into tissues, as well as by similarities in echo-genicity between different tissues. The present invention includes a system in which an intravascular probe actively transmits ultrasound that can then be detected by in-line piezoelectric transducers without reflection. This signal can be overlaid onto traditional B-mode or Doppler representation. Furthermore, the present invention includes a signal processing system that will display a real-time graphical representation of the vascular anatomy in order to assist the surgeon or procedural radiologist in the placement of central venous catheters.

20 Claims, 7 Drawing Sheets

Related U.S. Application Data

(60) Provisional application No. 61/872,903, filed on Sep. 3, 2013.

(56) References Cited

U.S. PATENT DOCUMENTS

| | | |
|---|---|---|
| 6,332,089 B1 | 12/2001 | Acker et al. |
| 6,425,865 B1 | 7/2002 | Salcudean et al. |
| 7,068,867 B2 | 6/2006 | Adoram et al. |
| 9,636,083 B2 | 5/2017 | Boctor et al. |
| 2004/0015087 A1 | 1/2004 | Boric-Lubecke et al. |
| 2004/0097805 A1* | 5/2004 | Verard ............... A61B 1/00071 600/428 |
| 2004/0236170 A1* | 11/2004 | Kim .................... A61B 17/11 600/16 |
| 2005/0228286 A1 | 10/2005 | Messerly et al. |
| 2005/0261591 A1 | 11/2005 | Boctor et al. |
| 2006/0074319 A1 | 4/2006 | Barnes et al. |
| 2007/0016068 A1 | 1/2007 | Grunwald et al. |
| 2009/0118612 A1* | 5/2009 | Grunwald ................ A61B 5/06 600/424 |
| 2011/0275890 A1 | 11/2011 | Wang et al. |
| 2014/0024928 A1* | 1/2014 | Boctor .................. A61B 10/02 600/424 |
| 2016/0192900 A1 | 7/2016 | Abdullah et al. |
| 2016/0235046 A1 | 8/2016 | Etienne-Cummings et al. |
| 2017/0188991 A1 | 7/2017 | Boctor et al. |

OTHER PUBLICATIONS

Verghese S.T., et al., "Ultrasound-guided Internal Jugular Venous Cannulation in Infants: A Prospective Comparison with the Traditional Palpation Method," Anesthesiology, Jul. 1999, vol. 91(1), pp. 71-77.

* cited by examiner

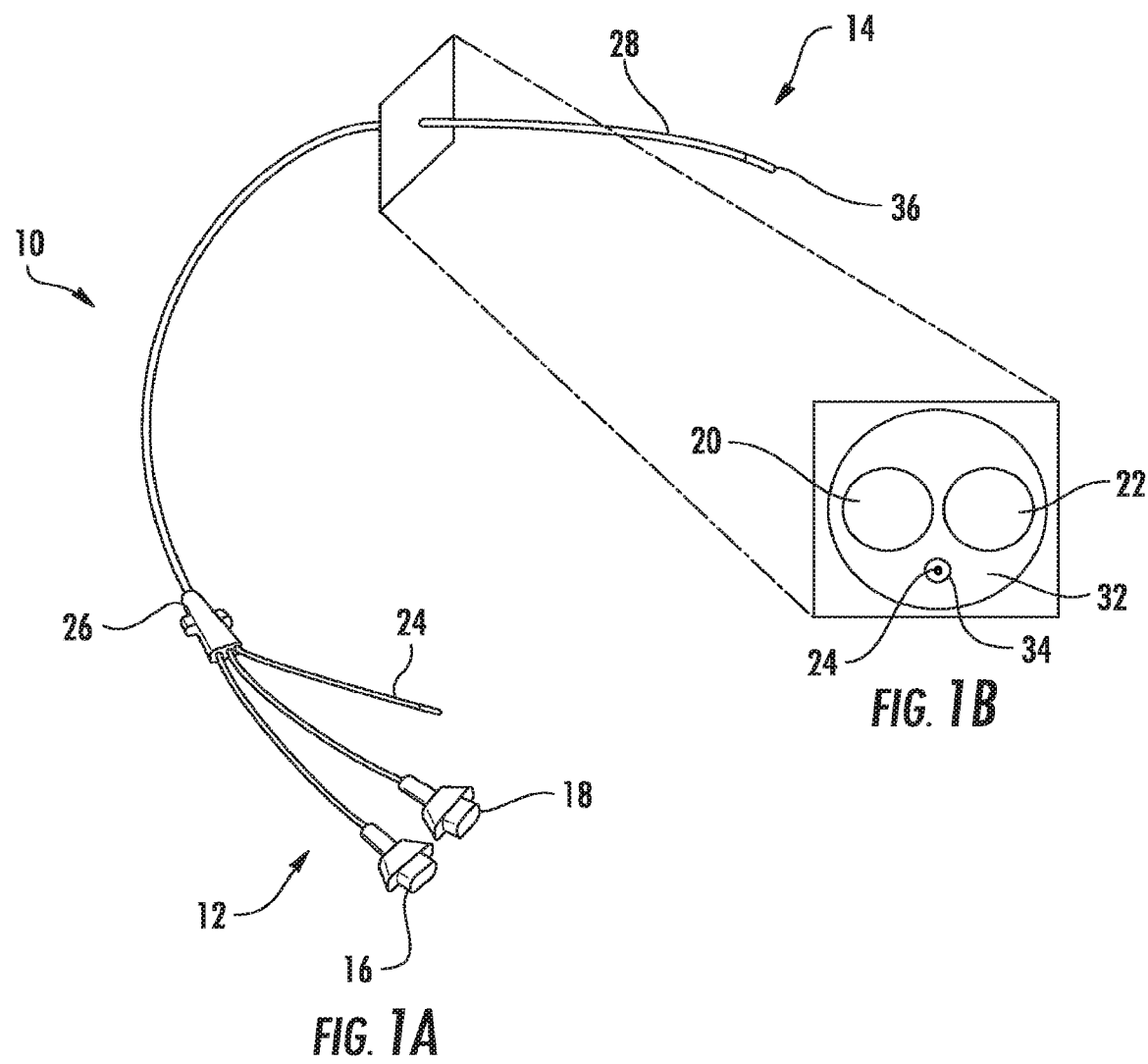

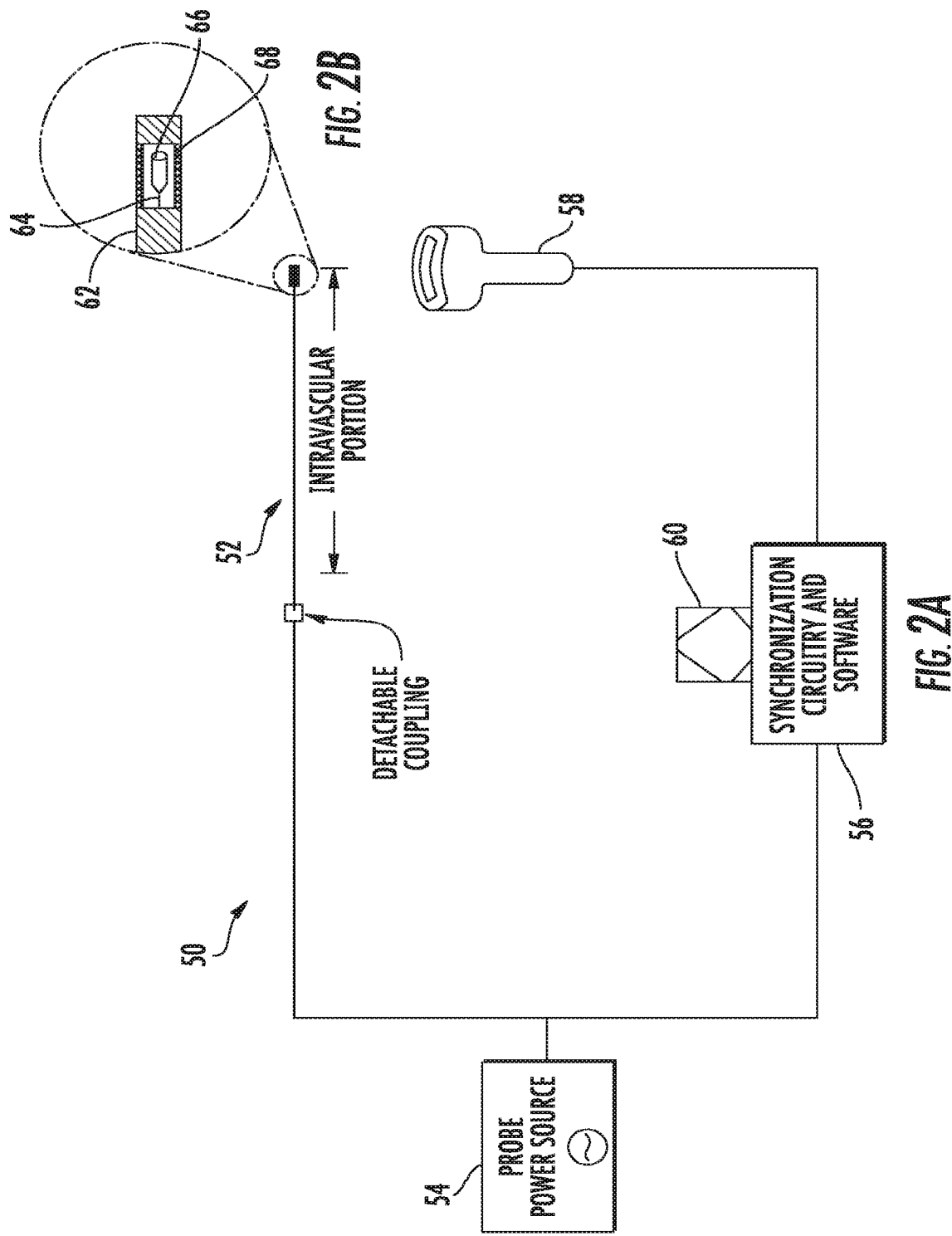

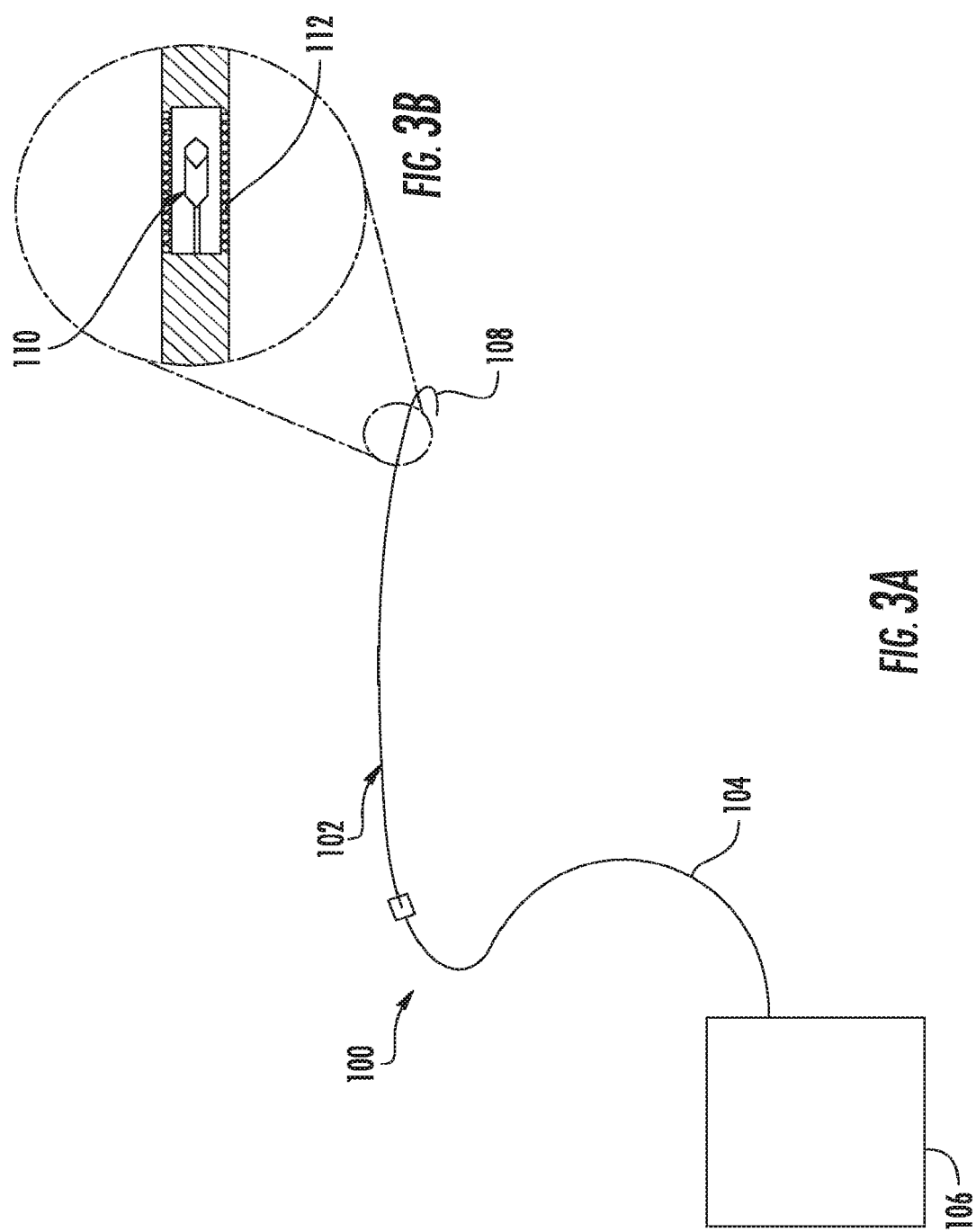

DEVICE FOR UTILIZING TRANSMISSION ULTRASONOGRAPHY TO ENABLE ULTRASOUND-GUIDED PLACEMENT OF CENTRAL VENOUS CATHETERS

CROSS REFERENCE TO RELATED APPLICATIONS

This application is a continuation of U.S. patent application Ser. No. 14/916,260, filed Mar. 3, 2016, which is a 35 U.S.C. § 371 U.S. national entry of International Application PCT/US2014/049353, having an international filing date of Aug. 1, 2014, which claims the benefit of U.S. Provisional Application No. 61/872,903, filed Sep. 3, 2013, the contents of each of the aforementioned applications is herein incorporated by reference in their entirety.

FIELD OF THE INVENTION

The present invention relates generally to medical imaging. More particularly, the present invention relates to a device for image guided placement of a central venous catheter.

BACKGROUND OF THE INVENTION

Central venous catheters have many uses and are used in patients of all ages, including pediatric patients. Central venous catheters are generally inserted using the Seldinger technique. First, a blunt guidewire is passed through a needle inserted into the vein. The progress and position of the guidewire can be monitored using fluoroscopy. After the guidewire is positioned, a stiff introducer is inserted, the guidewire is removed, and the catheter is passed into the vein within the introducer. Once the catheter is positioned, more fluoroscopic images are obtained to confirm correct placement of the catheter. However, the amount of radiation involved in this procedure is not ideal, particularly for small children.

Accordingly, there is a need in the art for an imaging device to guide placement of a central venous catheter that emits little to no ionizing radiation, especially for pediatric patients.

SUMMARY OF THE INVENTION

The foregoing needs are met, to a great extent, by the present invention which provides a system for intravascular transmission ultrasonography, including an intravascular probe having a proximal end and a distal end, wherein the intravascular probe is configured to produce ultrasonic energy. The system includes a catheter having a proximal end and a distal end, and also being configured to transmit ultrasonic energy. The system also includes a detection probe configured to detect ultrasonic energy from the intravascular probe and the catheter and a computing device configured to process and display information from the ultrasound probe.

In accordance with an aspect of the present invention, the intravascular probe includes a piezoelectric device. The piezoelectric device is disposed at a distal end of the intravascular probe. The catheter also includes a piezoelectric device that can be disposed at the distal end of the catheter. The detection probe takes the form of a blanket array, or alternately the detection probe takes the form of a single probe disposed on a robotic arm. The computing device can include a non-transitory computer readable medium. Additionally, the intravascular probe can take the form of a seldinger-type wire, and the catheter can take the form of a central venous catheter.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 1A illustrates a perspective view of a central venous catheter according to an embodiment of the present invention.

FIG. 1B illustrates a sectional view of the central venous catheter of FIG. 1A taken along a transverse axis of the catheter.

FIG. 2A illustrates a schematic diagram of a ultrasound imaging system for placement of a central venous catheter.

FIG. 2B illustrates a sectional view of a distal end of an intravascular probe, according to an embodiment of the present invention.

FIG. 3A illustrates a schematic diagram of a guide wire for a system for ultrasound imaging for placement of a central venous catheter, according to an embodiment of the present invention.

FIG. 3B illustrates a sectional view of a portion of a guide wire of FIG. 3B, according to an embodiment of the present invention.

DETAILED DESCRIPTION

Figure 4A:
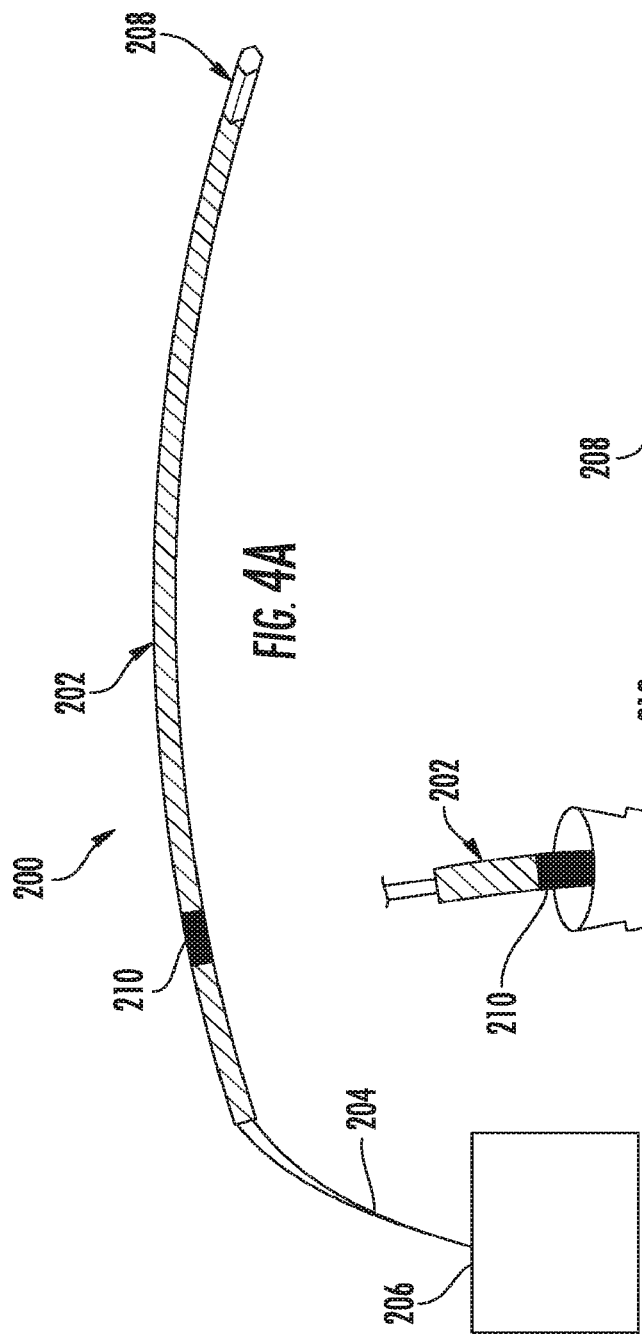
FIG. 4A illustrates a schematic diagram of a stylet for a system for ultrasound imaging for placement of a central venous catheter, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a system to enable ultrasound-guided placement of a central venous catheter (CVC). Ultrasound is typically performed with the use of an external transcutaneous probe that emits ultrasonic energy and measures the timing of reflected waves, thus allowing measurement of fluid flow or formation of a two-dimensional image. Clinically, the modality is limited by attenuation of the signal with increasing depth of penetration of the ultrasound into tissues. The present invention includes a system in which an intravascular probe actively transmits ultrasound that can then be detected by in-line piezoelectric transducers without reflection. This signal can be overlaid onto traditional B-mode or Doppler representation. Furthermore, the present invention includes a signal processing system that will display a real-time graphical representation of the vascular anatomy in order to assist the surgeon or procedural radiologist in the placement of central venous catheters.

A system for transmission ultrasonography guided placement of a central venous catheter or other similar device, according to the present invention, includes a Seldinger-style wire configured to be capable of producing ultrasonic energy after intravascular placement with an introducer sheath. The system also includes a catheter also configured to be capable of producing ultrasonic energy after intravascular placement. Additionally, the system includes a detection probe of piezoelectric transducers, either in a blanket array or a single probe on a robotic arm and processing software that permits a stylized representation of the intravascular anatomy and wire/catheter location.

FIG. 1A illustrates a perspective view of a central venous catheter with ultrasonic capabilities, according to an embodiment of the present invention. As illustrated in FIG. 1A the central venous catheter 10 includes a proximal end 12 and a distal end 14. The proximal end 12 of the central venous catheter 10 includes at least two fluid ports 16, 18. These fluid ports are in fluid communication with fluid lumens 20, 22, illustrated in FIG. 1B. The fluid lumens 20, 22 extend from the proximal end 12 to the distal end 14 of the catheter 10. The fluid ports 16, 18 and fluid lumens 20, 22 are configured for the delivery of any substance known to or conceivable by one of skill in the art. The fluid ports 16, 18 can take any suitable form known to or conceivable by one of skill in the art, and the lumens 20, 22 can have equivalent diameters, as illustrated in FIG. 1B or can have different diameters, as is known to or conceivable by one of skill in the art. The catheter 10 also includes an electrode 24. The electrode 24 extends from the proximal end 12 to the distal end 14 of the catheter 10. The electrode 24 can have a proximal end 26 and a distal end 28. The proximal end 26 of the electrode 24 includes a detachable coupling 30, or any other suitable coupling known to or conceivable by one of skill in the art. The electrode 24 extends through the catheter 10, as illustrated in FIG. 1B. The electrode 24 can be embedded in the wall 32 of the catheter 10 or can be disposed within a third lumen 34 extending through the length of the catheter 10. A piezoelectric transducer 36 is embedded in or near the distal end 28 of the electrode 24.

FIG. 2A illustrates a schematic diagram of a system in accordance with the present invention. The system 50 includes an intravascular probe 52 configured to transmit detectable signals to ensure correct positioning of the intravascular probe 52. The intravascular probe 52 includes an intravascular portion 53, and can be configured to resemble a Seldinger-type wire. The intravascular probe 52 is coupled, preferably detachably to a power source 54. In turn the intravascular probe 52 is also coupled to a computing device 56 capable of receiving signal from the intravascular probe 52. While the probe 52 is shown in FIG. 2A, the system also includes a central venous catheter, as described in FIGS. 1A and 1B. The central venous catheter can be connected to the system in the same way as the intravascular probe 52. The system 50 also includes a standard handheld ultrasound probe 58, or any other suitable ultrasound device known to or conceivable by one of skill in the art. The ultrasound probe 58 is connected to the computing device 56, which is also capable of receiving signal from the ultrasound probe 58. The computing device 56 is further configured to overlay transmission from the intravascular probe 52 onto a B-mode ultrasound image 60 obtained using the ultrasound probe 58. The computing device 56 can included synchronization circuitry and software in order to implement the display of the information from the ultrasound probe 58 and the intravascular probe 52. Alternately, the computing device 56 can be wirelessly or wire networked to other computing devices capable of processing this information, such as a server. The computing device 56 can therefore take any form known to or conceivable by one of skill in the art as suitable for this purpose, such as but not limited to a PC, tablet computing device, or smartphone. The synchronization circuitry and software can take the form of a non-transitory computer readable medium.

FIG. 2B illustrates a distal end 62 of the intravascular probe 52. The distal end of the intravascular probe 52 includes an electrode 64, a piezoelectric transducer 66, and a nitinol wrapping 68 disposed around the electrode 64 and the piezoelectric transducer 66. As noted above, the distal end of the intravascular probe is inserted into the vasculature of the patient, and is detected by the ultrasound probe.

FIG. 3A illustrates a schematic diagram of a guide wire for a system for ultrasound imaging for placement of a central venous catheter, according to an embodiment of the present invention. As illustrated in FIG. 3A, a system for ultrasound imaging for placement of a central venous catheter 100, includes a guidewire 102. The guide wire 102 is configured to be threaded into the vasculature of a patient, ahead of placement of a central venous or other catheter. The guide wire 102 can take any form known to one of skill in the art. However, preferably the guide wire takes the form of a helically wrapped, shape memory metal, such as nitinol. The guide wire 102 is coupled to a detachable coupling 104. The detachable coupling 104 connects the guide wire 102 to a power/circuitry box 106. When the guide wire 102 is connected to the power/circuitry box 106, the guide wire 102 acts as a transmission ultrasonography probe. While FIG. 3A illustrates a detachable coupling 104 to couple the guide wire 102 to the power/circuitry box 106, the guide wire 102 could be coupled directly to the power/circuitry box 106 with an adapter, or any other mode of attachment known to or conceivable by one of skill in the art. The guide wire 102 can also include a "j" tip or any other suitable distal terminus known to or conceivable by one of skill in the art.

FIG. 3B illustrates a sectional view of a portion of a guide wire of FIG. 3B, according to an embodiment of the present invention. As illustrated in FIG. 3B, a piezoelectric transducer assembly 110 is positioned just proximal to the distal end of the guide wire 102, i.e. just proximal of the "j" tip. The piezoelectric transducer assembly includes a piezoelectric transducer and two insulated electrodes. As illustrated in FIG. 3B the helical coils 112 of the guide wire 102 surround the piezoelectric transducer assembly 110. It should be noted that when the guide wire 102 is coupled to the power/circuit box 106 it serves as a transmission ultrasonography probe, and when it is not connected the guide wire 102 acts passively as a fully functional guide wire.

FIG. 4A illustrates a schematic diagram of a stylet for a system for ultrasound imaging for placement of a central venous catheter, according to an embodiment of the present invention. As illustrated in FIG. 4A the system 200 includes a stylet 202, a detachable coupling 204, and a power/circuit box 206. The detachable coupling 204 and the power/circuit box 206 can be separate from those described with respect to FIG. 3A, or the same detachable coupling 204 and power/circuit box 206 can be used with both the guide wire and the stylet. When the stylet 202 is connected to the power/circuitry box 206, the stylet 202 acts as a transmission ultrasonography probe. While FIG. 4A illustrates a detachable coupling 204 to couple the stylet 202 to the power/circuitry box 206, the stylet 202 could be coupled directly to the power/circuitry box 206 with an adapter, or any other mode of attachment known to or conceivable by one of skill in the art. The stylet 202 includes an outer diameter that is less than an internal lumen diameter of a catheter used for a central venous catheter, or any other catheter placement with which this system may be used. The stylet 202 is also configured to be sufficiently flexible in order to follow a path of the catheter through the vasculature. The stylet 202 includes a piezoelectric transducer assembly 208 at its distal end and a marking 210 adjacent to its proximal end, in order to have proper stylet 202 placement with respect to a catheter.

Figure 4C:
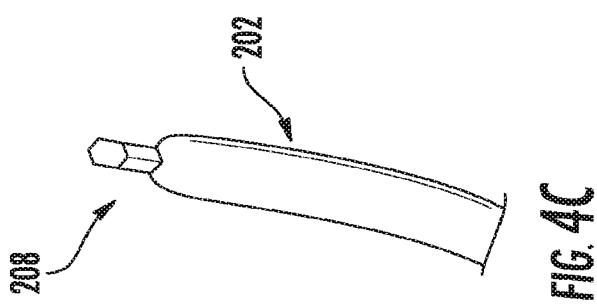
FIGS. 4B and 4C illustrate a miniature piezoelectric transducer disposed at a tip of the stylet of FIG. 4A, according to an embodiment of the present invention.
Figure 4B:
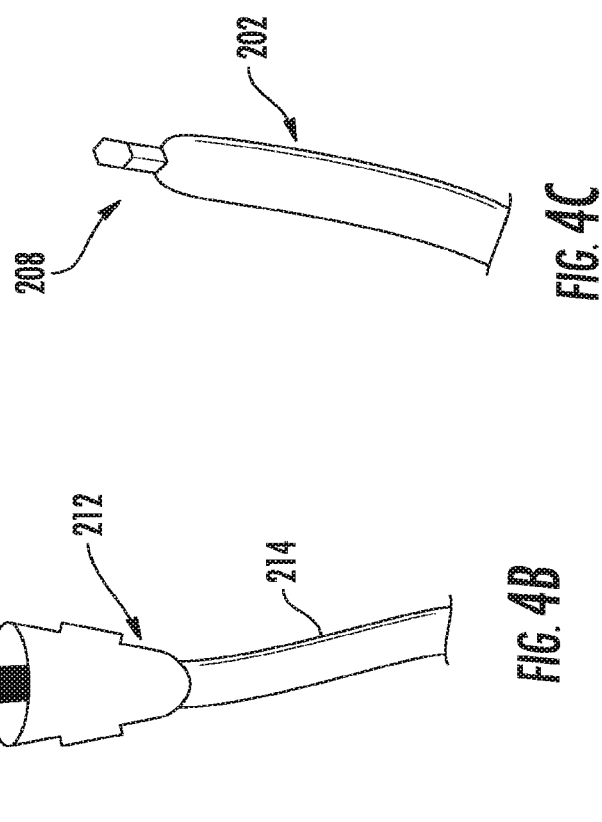

FIG. 4B illustrates a proximal end of the stylet of FIG. 4A being passed through a catheter hub and 4C illustrates a miniature piezoelectric transducer disposed at a tip of the stylet of FIG. 4A, according to an embodiment of the present invention. As illustrated in FIG. 4A, a marking 210 is placed near the proximal end of the stylet. This marking 210 is placed such that alignment of the marking with a rim of the catheter port 212 places the piezoelectric transducer assembly 208 at a distal tip of the catheter 214. FIG. 4C illustrates a piezoelectric transducer assembly 208 of the stylet 202. Similarly to the guide wire, the piezoelectric transducer assembly of the stylet 202 includes a piezoelectric transducer and two insulated electrodes.

It should be noted that a kit according to an embodiment of the present invention can include both a guide wire and a stylet, as described above, in order to facilitate performance of a central venous catheter, or other catheter, in accordance with the Seldinger technique. Other techniques for catheter placement could also be used, and therefore, the guide wire and stylet could also be used independently of one another. The guide wire and stylet are configured for use with any ultrasound system available for use. An adapter for connection of the guide wire and/or stylet could also be included with a kit, according to an embodiment of the present invention.

Figure 5:
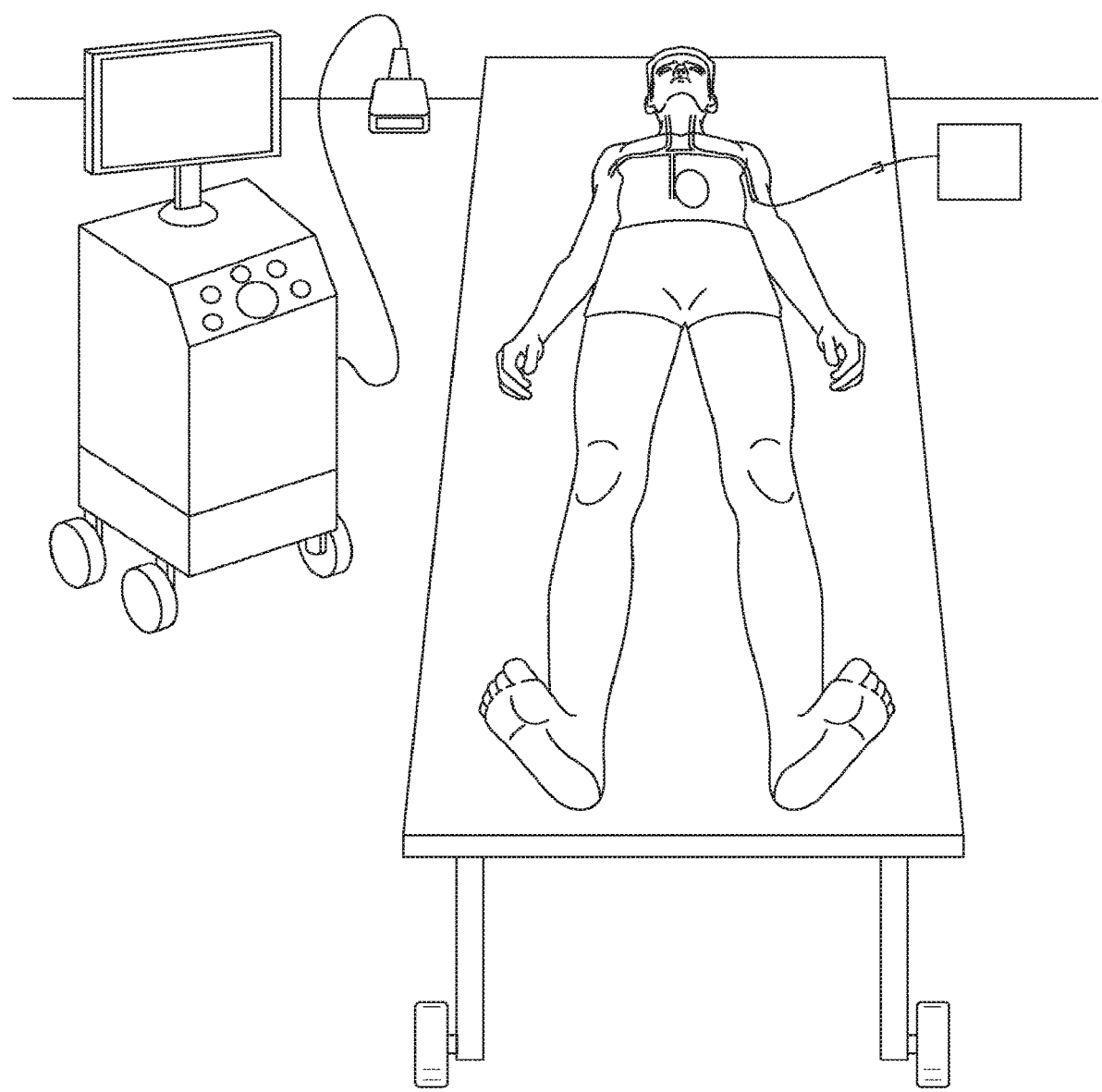
FIG. 5 illustrates a diagram of a proposed clinical use, according to an embodiment of the present invention.

FIG. 5 illustrates a diagram of a proposed clinical use, according to an embodiment of the present invention. As illustrated in FIG. 5 a small infant is positioned on an operating room table. A guide wire and/or a catheter with stylet is placed through a left subclavian vein of the infant. The tip of the guide wire and/or stylet is disposed in a superior vena cava, for central venous catheter placement. Other placement could be contemplated with respect to placement of other types of catheters using the system of the present invention. A commercially available ultrasound system with B-mode imaging capabilities is used to detect readout from the guide wire and or the stylet. The piezoelectric transducer assembly of the guide wire and stylet described above is configured only to transmit when it hears output from the ultrasound machine. There is no integration of the system of the present invention with the commercially available ultrasound system, and there is no need for tracking or registration of any component therein. The system of the present invention can therefore be used with any available ultrasound machine, making it very versatile.

Figure 6:
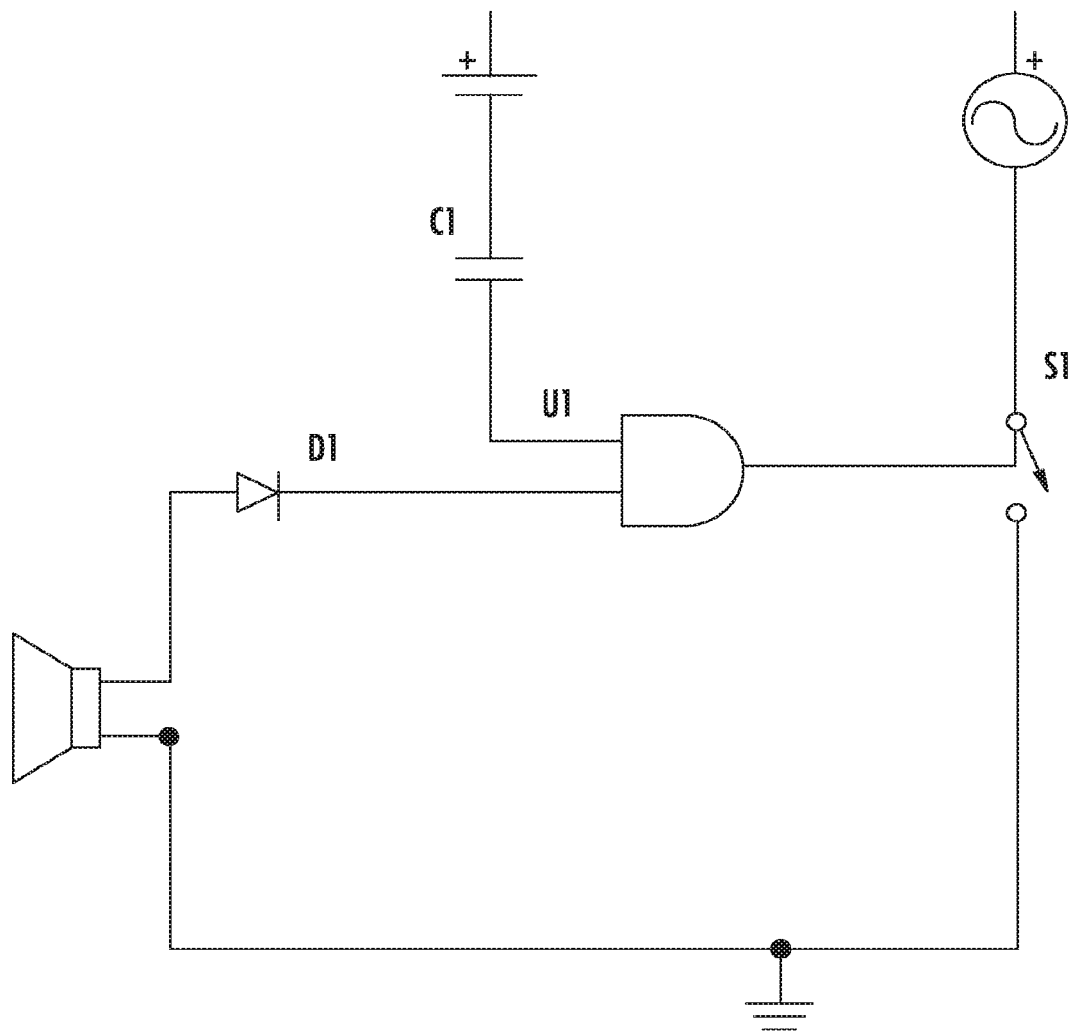
FIG. 6 illustrates a schematic diagram of a circuit according to an embodiment of the present invention.

FIG. 6 illustrates a schematic diagram of a circuit according to an embodiment of the present invention. As illustrated in FIG. 6, a piezoelectric transducer of the present invention is stimulated in a detection frequency bandwidth by an ultrasound probe. This interaction between the sound waves emitted by the ultrasound probe and the piezoelectric transducer creates an oscillating voltage. A D1 rectifier converts the oscillating voltage into a direct current and charges capacitor C1. U1 and logic gate detect charged capacitor C1 and signal input after stimulation. Voltage controlled switch S1 is closed by U1 output and drives alternating current across the piezoelectric transducer, via the insulated electrodes, described above with respect to the guide wire and stylet. The current across the piezoelectric transducer creates an ultrasound wave. Switch S1 closes when capacitor C1 is discharged under threshold voltage of AND gate, creating a refractory period during which the circuit resets to listen for a next pulse from the ultrasound wand.

EXAMPLE

The follow exemplary implementation of an ultrasound probe according to an embodiment of the present invention is included merely as an example, and is not considered to be limiting. Any other implementation known to or conceivable by one of skill in the art could also be used.

Figure 7A:
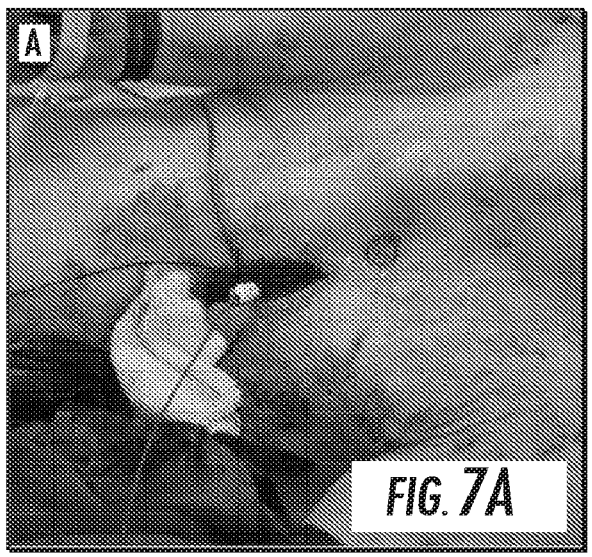
FIGS. 7A-7D illustrate an exemplary implementation of the present invention.

An intravascular transmission ultrasonography probe was custom fabricated, in which a piezoelectric transducer actively emits signal that can be detected by a standard handheld probe, rather than relying solely on reflected acoustic waves to create an image. A miniaturized element was integrated into a flexible catheter that was introduced by vascular sheath into the central veins of an immature pig, as illustrated in FIG. 7A.

Figure 7B:
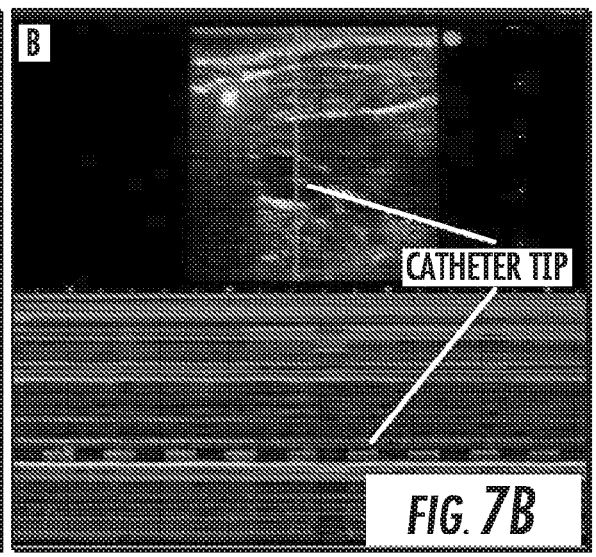
Figure 7C:
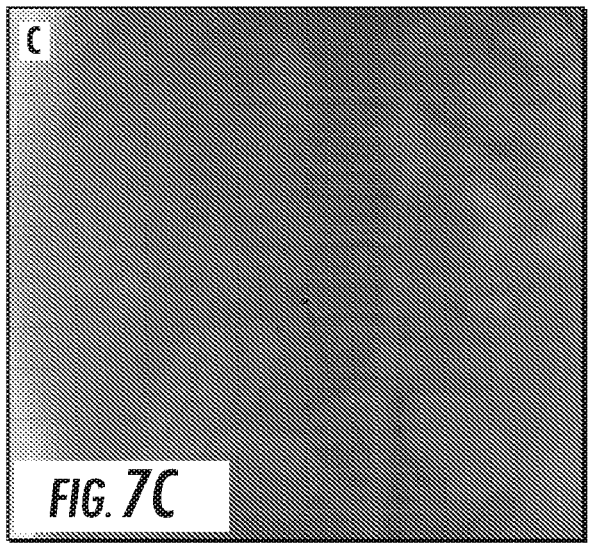
Figure 7D:
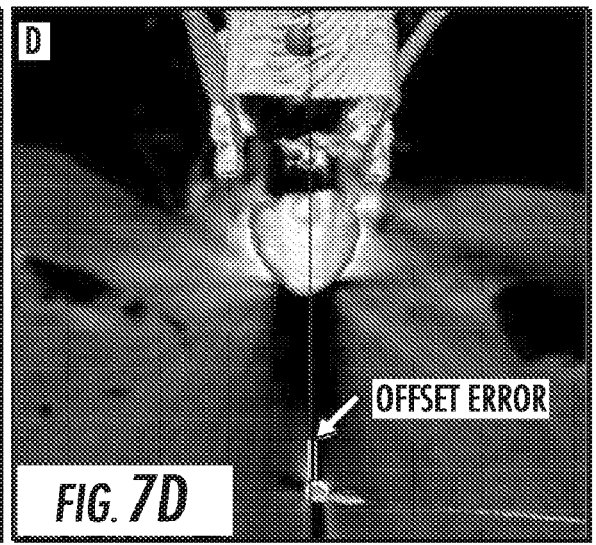

Catheter tip location was noted to blink on B-mode ultrasound with a standard handheld ultrasound probe, as illustrated in FIG. 7B. Tip location along the vessel axis was estimated using the probe freehand and marked with radiopaque beads within 1 cm of its superior/inferior position by digital fluoroscopy, as illustrated in FIG. 7C. With the probe on a fixed passive arm, 3-dimensional tomographic reconstructions demonstrated the catheter tip within 0.5-3 mm of the mid-plane of the ultrasound image, as illustrated in FIG. 7D. An intravascular transmission ultrasonography probe therefore safely allowed accurate and precise localization of relevant venous anatomy in a large animal model.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of placing a central venous catheter into a patient, comprising:

providing a guidewire to be positioned into a superior vena cava of the patient,
   wherein the guidewire includes a first piezoelectric transducer at a distal end of the guidewire,
   wherein the first piezoelectric transducer is configured to be stimulated in a detection frequency bandwidth associated with sounds waves emitted by an ultrasound probe,
   wherein the first piezoelectric transducer is configured to create a first oscillating voltage based on being stimulated in the detection frequency bandwidth,
   wherein the first piezoelectric transducer is configured to create first ultrasound pulses based on the first oscillating voltage,
   wherein the first piezoelectric transducer is configured to transmit the first ultrasound pulses,
   wherein the first ultrasound pulses are received by the ultrasound probe and processed to indicate a location of the first piezoelectric transducer, and
   wherein an indication of the location of the first piezoelectric transducer is displayed as a first signal overlaid on an ultrasound image; and
providing the central venous catheter to be positioned over the guidewire and into the superior vena cava,
   wherein the guidewire is to be removed based on the central venous catheter being positioned in the superior vena cava,
   wherein a distal end of the central venous catheter includes a second piezoelectric transducer,
   wherein the second piezoelectric transducer is configured to be stimulated in the detection frequency bandwidth associated with the sound waves emitted by the ultrasound probe,
   wherein the second piezoelectric transducer is configured to create a second oscillating voltage based on being stimulated in the detection frequency bandwidth,
   wherein the second piezoelectric transducer is configured to create second ultrasound pulses based on the second oscillating voltage,
   wherein the second piezoelectric transducer is configured to transmit the second ultrasound pulses,
   wherein the second ultrasound pulses are received by the ultrasound probe and processed to indicate a location of the second piezoelectric transducer, and
   wherein an indication of the location of the second piezoelectric transducer is displayed as a second signal overlaid on the ultrasound image.

2. The method of claim 1, wherein the ultrasound probe is an external probe.

3. The method of claim 1, wherein the guidewire is a Seldinger-type wire.

4. The method of claim 1, further comprising:
providing an introducer sheath for intravascular placement prior to providing the guidewire to be positioned in the superior vena cava.

5. The method of claim 1, wherein the ultrasound image is a B-mode image associated with the ultrasound probe.

6. A device, comprising:
a stylet comprising a first piezoelectric transducer at a distal end of the stylet,
   wherein the stylet is configured to be positioned into a superior vena cava of a patient, and
   wherein the first piezoelectric transducer is configured to:
      be stimulated in a detection frequency bandwidth associated with sounds waves emitted by an ultrasound probe,
      create a first oscillating voltage based on being stimulated in the detection frequency bandwidth,
      create first ultrasound pulses based on the first oscillating voltage, and
      transmit the first ultrasound pulses to the ultrasound probe,
         wherein the first ultrasound pulses are processed to indicate a location of the first piezoelectric transducer, and
         wherein an indication of the location of the first piezoelectric transducer is displayed as a first signal overlaid on an ultrasound image; and
a central venous catheter comprising a second piezoelectric transducer at a distal end of the central venous catheter,
   wherein the central venous catheter is configured to be positioned over the stylet and into the superior vena cava,
   wherein the stylet is to be removed based on the central venous catheter being positioned in the superior vena cava, and
   wherein the second piezoelectric transducer is configured to:
      be stimulated in the detection frequency bandwidth,
      create a second oscillating voltage based on being stimulated in the detection frequency bandwidth,
      create second ultrasound pulses based on the second oscillation voltage, and
      transmit the second ultrasound pulses to the ultrasound probe,
         wherein the second ultrasound pulses are processed to indicate a location of the second piezoelectric transducer, and
         wherein an indication of the location of the second piezoelectric transducer is displayed as a second signal overlaid on the ultrasound image.

7. The device of claim 6, wherein the ultrasound probe is an external probe.

8. The device of claim 6, wherein the ultrasound image is a B-mode image associated with the ultrasound probe.

9. The device of claim 6, wherein the stylet is configured to be connected to a power source via a detachable coupling.

10. The device of claim 9, wherein the power source is connected to synchronization circuitry and software.

11. A method for ultrasound-guided placement of a central venous catheter into a patient, comprising:
receiving, by a device, a first set of sound waves transmitted from an external ultrasound probe,
   wherein a guidewire or stylet of the device is configured to be positioned in a superior vena cava of the patient, and
   wherein a first piezoelectric transducer of the device is configured to be stimulated in a detection frequency bandwidth associated with the first set of sound waves transmitted by the external ultrasound probe;
creating, by the device, a first oscillating voltage based on the first piezoelectric transducer being stimulated in the detection frequency bandwidth;
creating, by the device, a second set of sound waves based on the first oscillating voltage;

transmitting, by the device, the second set of sound waves for a real-time graphical representation of a vascular anatomy associated with the patient,
  wherein the real-time graphical representation of the vascular anatomy includes a representation of a location of the first piezoelectric transducer overlaid on a B-mode image associated with the external ultrasound probe;
receiving, by the device, a third set of sound waves transmitted from the external ultrasound probe,
  wherein the device comprises the central venous catheter,
  wherein the central venous catheter is configured to be positioned in the superior vena cava, and
  wherein a second piezoelectric transducer of the device is configured to be stimulated in the detection frequency bandwidth,
creating, by the device, a second oscillating voltage based on the second piezoelectric transducer being stimulated in the detection frequency bandwidth;
creating, by the device, a fourth set of sound waves based on the second oscillating voltage; and
transmitting, by the device, the fourth set of sound waves for the real-time graphical representation of the vascular anatomy,
  wherein the real-time graphical representation of the vascular anatomy includes a representation of a location of the second piezoelectric transducer overlaid on the B-mode image.

12. The method of claim 11, wherein the guidewire or stylet is an intravascular ultrasound probe.

13. The method of claim 11, wherein the guidewire or stylet is connected to a power source via a detachable coupling.

14. The method of claim 1, wherein the central venous catheter is connected to a power source via a detachable coupling.

15. The method of claim 1, wherein the central venous catheter is flexible.

16. The device of claim 6, wherein the central venous catheter is configured to be connected to a power source via a detachable coupling.

17. The method of claim 11, wherein the central venous catheter is connected to a power source via a detachable coupling.

18. The method of claim 1, wherein the first piezoelectric transducer is in-line with the ultrasound probe.

19. The device of claim 6, wherein the first piezoelectric transducer is configured to be in-line with the ultrasound probe.

20. The device of claim 6, further comprising:
  a detachable coupling configured to be coupled to a power source.

* * * * *